(12) United States Patent
Imae et al.

(10) Patent No.: US 8,927,658 B2
(45) Date of Patent: Jan. 6, 2015

(54) FLUORESCENT HYBRID OF DENDRIMER AND GRAPHENE OXIDE

(71) Applicants: Toyoko Imae, Taipei (TW); Ampornphan Siriviriyanun, Taipei (TW)

(72) Inventors: Toyoko Imae, Taipei (TW); Ampornphan Siriviriyanun, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 136 days.

(21) Appl. No.: 13/622,369

(22) Filed: Sep. 19, 2012

(65) Prior Publication Data

US 2014/0080980 A1 Mar. 20, 2014

(51) Int. Cl.
*C08L 77/00* (2006.01)
*A61K 45/00* (2006.01)

(52) U.S. Cl.
USPC ........... 525/435; 428/220; 524/495; 524/496; 524/538; 525/420

(58) Field of Classification Search
USPC .................. 525/420, 435; 524/495, 496, 538; 428/220
See application file for complete search history.

(56) References Cited

U.S. PATENT DOCUMENTS

2012/0003155 A1 1/2012 Kannan et al.
2012/0107593 A1 5/2012 Luo et al.
2012/0177593 A1 7/2012 Baker, Jr. et al.

OTHER PUBLICATIONS

Derwent-Acc-No. 2010-D54789 (CN 101670108, Mar. 17, 2010).*
Zhang, L.; Xia, J.; Zhao, Q.; Liu, L.; Zhang, Z. Functional Graphene Oxide as a Nanocarrier for Controlled Loading and Targeted Delivery of Mixed Anticancer Drugs. Small. Feb. 2010, 6(4), 537-544.
Sun, X.; Liu, Z.; Welsher, K., Robinson, J.T.; Goodwin, A.; Zaric, S.; Dai, H. Nano-Graphene Oxide for Cellular Imaging and Drug Delivery. Nano Res. Jul. 2008, 1, 203-212.
Zhou, I.; Wang, W.; Tang, J.; Zhou, J.H.; Jiang, H.J.; Shen, J. Graphene oxide noncovalent photosensitizer and its anticancer activity in vitro. Chem. Eur. J. Oct. 2011, 17, 12084-12091.
Tian, B.; Wang, C.; Zhang, S.; Feng, L; Liu, Z. Photothermally enhanced photodynamic therapy delivered by nano-graphene oxide. ACS Nano. Aug. 2011, 5, 7000-7009.
Yang, Y.; Zhang, Y.M.; Chen, Y.; Zhao, D.; Chen, J.T.; Liu, Y. Construction of a graphene oxide based noncovalent multiple nanosupramolecualr assembly as a scaffold for drug delivery. Chem. Eur. J. Apr. 2012, 18, 4208-4215.

* cited by examiner

*Primary Examiner* — Ana Woodward
(74) *Attorney, Agent, or Firm* — Jianq Chyun IP Office

(57) ABSTRACT

The present invention relates to a fluorescent hybrid material of dual functionality. The hybrid material may function as the fluorescence marker and as the attacking drug at the same time for biomedical applications.

11 Claims, 11 Drawing Sheets

US 8,927,658 B2

FLUORESCENT HYBRID OF DENDRIMER AND GRAPHENE OXIDE

BACKGROUND OF THE INVENTION

1. Field of the Invention

The present invention generally relates to a hybrid material. More particularly, the present invention relates to a fluorescent hybrid material of graphene oxide and dendrimers.

2. Description of Related Art

Graphene oxide (GO) is an oxidized graphene bulk material, which is composed of a graphene-like sheet chemically functionalized with oxygen-including groups such as hydroxyl, carboxylic acid and epoxide. It has been reported that the functionalization of GO leads to the change in the electrical and optical properties. As provided in this invention, hybrid materials of graphene oxide may be new promising materials for biological and medical applications including cellular imaging, drug delivery, and photodynamic therapy.

Dendrimers are highly branched molecules that are typically symmetric around the core, and often adopt spherical three-dimensional morphologies. Poly(amidoamine) (PAMAM) dendrimers generally have multiply-functionalized peripheral surfaces, high degree of molecular uniformity, well-defined molecular weight, and specified size and shape. The manufacturing processes of PAMAM dendrimers include a series of repetitive steps starting with a central initiator core. Each set of repetitive steps causes an interior layer (i.e. a "generation") composed of repeating units added to the core, leading to the polymer with a larger molecular diameter, twice the number of reactive surface sites, and approximately double the molecular weight of the polymer of the preceding generation. Dendrimers have attracted wide interests in the field of chemistry and biology, especially in applications like drug delivery, gene therapy and chemotherapy.

PAMAM dendrimers also have a strong fluorescence emission, which makes them become potential imaging agents. The oxidation of tertiary amine groups of PAMAM dendrimers is the main contribution to the fluorescence phenomenon. Due to the characteristic fluorescence, the cellular uptake behaviour of PAMAM dendrimers may be directly analyzed by fluorescence microscopy together by flow cytometry, without additional fluorescence labelling.

However, for biological or biomedical applications, the biocompatibility of the dendrimers, including cytotoxicity, biodegradable capability and metabolization in vivo, has to be balanced with the water solubility and functionality of the dendrimers.

SUMMARY OF THE INVENTION

The present invention relates to a novel hybrid material of dual functionality. The hybrid material may function as the fluorescence marker or probe and as the attacker at the same time.

The present invention is directed to a hybrid material. The hybrid material includes at least a hydroxyl-terminated fourth-generation (G-4) poly(amidoamine) (PAMAM) dendrimer (DEN-OH) and folic acid (FA) chemically bound on graphene oxide (GO). The hybrid material is prepared by mixing the DEN-OH and GO under stirring at room temperature, adding N,N'-dicyclohexylcarbodiimide (DCC) and 4-dimethylaminopyridine (DMAP) to a mixture of the DEN-OH and GO under stirring at room temperature for esterification to form an intermediate GO/DEN-OH that is the DEN-OH bound on GO, adding N-hydroxysuccinimide (NHS) and 1-[3-(dimethylamino)propyl]-3-ethylcarbodiimide hydrochloride (EDC) to an aqueous suspension of the intermediate GO/DEN-OH, and adding folic acid to a mixture of NHS, EDC and the aqueous suspension of the intermediate GO/DEN-OH under stirring at room temperature to obtain the hybrid material.

The present invention provides nano-hybrid materials, which exhibit two-photon fluorescence emission and is able to generate reactive oxygen species upon radiation.

In order to make the above and other features and advantages of the present invention more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

Common reference numerals are used throughout the drawings and the detailed description to indicate the same elements. The present invention will be more apparent from the following detailed description taken in conjunction with the accompanying drawings.

DESCRIPTION OF THE EMBODIMENTS

The present invention provides new hybrid materials including PAMAM dendrimers bound on graphene oxide (GO). In the present invention, a hydroxyl-terminated fourth-generation (generation 4, G-4) PAMAM dendrimer (DEN-OH) and folic acid (FA) are chemically bound on graphene oxide (GO) to form a hybrid material.

Such hybrid materials may target specifically to the cells with folate receptors, via the bound folic acid. Moreover, the ability of the hybrid materials to generate reactive oxygen species under laser irradiation makes them potential agents for photodynamic therapy.

For lowering the cytotoxicity, this invention adopts hydroxyl-terminated PAMAM dendrimers, instead of toxic amine-terminated dendrimer, for the preparation of the hybrid material. The OH-terminated PAMAM dendrimer is attached on graphene oxide by covalent-bonding between the —COOH group of GO and hydroxyl groups of the OH-terminated PAMAM dendrimer. Folic acid is independently attached on graphene oxide through reaction between the —COOH group of GO and NH$_2$ group of folic acid. For the prepared hybrid material of this invention, graphene oxide is a carrier platform loading dendrimers as its suspender in water and folic acid as an attacker to the target cancer cells. The prepared hybrid material of this invention is water dispersible. As the drug delivery system, the drugs are loaded on graphene oxide or the bound dendrimers, and many drugs may be are carried at the same time to the target site.

Since the oxygen-doped PAMAM dendrimer in the prepared hybrid material of this invention has fluorescence, no additional dyes or fluorescent labels are required for the present hybrid material, which is beneficial because additional dyes often increase toxicity. Owing to the PAMAM dendrimer, the hybrid materials exhibit two photon absorption properties and, upon laser irradiation, generate reactive oxygen species that are capable of attacking the cells.

EXPERIMENTAL SECTION

Binding of Hydroxyl-Terminated PAMAM Dendrimer (DEN-OH) and Folic Acid (FA) on Graphene Oxide (GO)

GO is an oxidized graphene graphene sheet with oxidized groups like hydroxyl, carboxylic acid and epoxide, and the content or the numbers of oxidized groups of GO depend on the degree of oxidation. Fourth generation OH-terminated PAMAM dendrimer (G-4 DEN-OH) has a molecular weight of 14,277 Da, with the molecular formula: $C_{622}H_{1184}N_{186}O_{188}$, having terminal group: 64.

Figure 1:
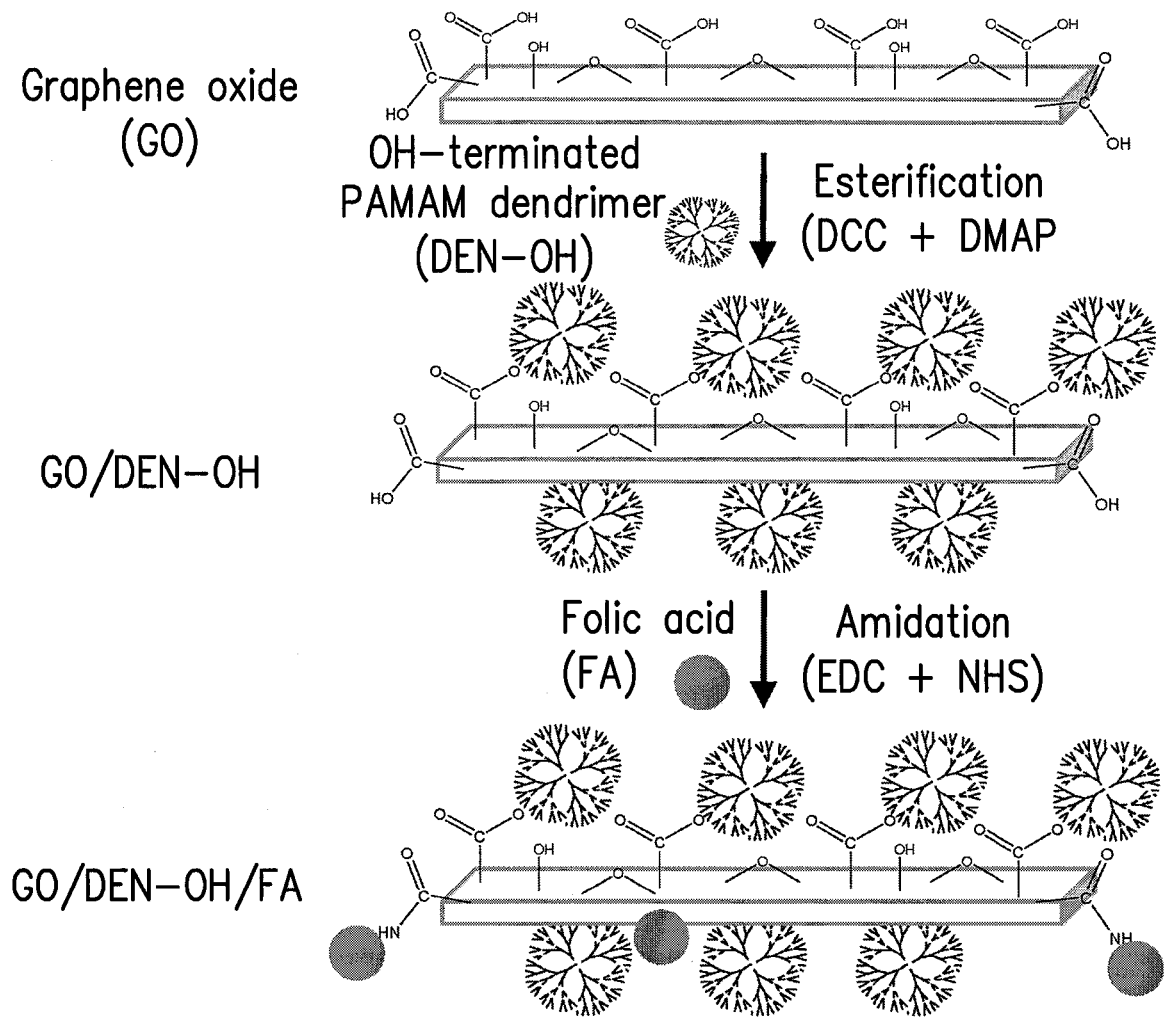
FIG. 1 shows the reaction scheme of OH-terminated PAMAM dendrimer (DEN-OH) and folic acid (FA) bound on graphene oxide (GO) according to one embodiment of the present invention.

As described in FIG. 1, DEN-OH and folic acid are attached to GO by using condensing agents for esterification and amidation, respectively.

The solvent in the methanol solution (10 wt %, 1 cm$^3$) of DEN-OH was evaporated and the residue was dissolved in dimethylformamide (DMF) (50 cm$^3$). An aqueous dispersion (4 cm$^3$) of GO was centrifuged, the supernatant was removed and the centrifugate was dispersed in DMF (4 cm$^3$). A DMF solution (0.2 wt %, 6 cm$^3$) of dendrimer was mixed with the DMF solution (10 wt %, 4 cm$^3$) of GO under stirring at room temperature. Subsequently, after N,N'-dicyclohexylcarbodiimide (DCC) (ranging from 3.7 mg to 18.5 mg) and 4-dimethylaminopyridine (DMAP) (about one tenth of DCC) were added, the mixture was further vigorously stirred at room temperature for 3 days to allow the esterification. The dispersion was centrifuged, and the centrifugate (GO/DEN-OH) was rinsed several times with DMF and then redispersed in water.

The synthesized GO/DEN-OH/FA hybrids may have different concentrations of DEN-OH. For the GO/DEN-OH/FA hybrid having DEN-OH=18 µM, the relative ratio of GO:DEN-OH:FA=0.55 mg:2.5 mg:0.45 mg. For the GO/DEN-OH/FA hybrid having DEN-OH=90 the relative ratio of GO:DEN-OH:FA=0.55 mg:12.8 mg:0.45 mg. That is, the hybrid material comprising 50-256 parts by weight of hydroxyl-terminated poly(amidoamine) (PAMAM) dendrimer (DEN-OH), 9 parts by weight of folic acid (FA), and 11 parts by weight graphene oxide (GO); wherein the DEN-OH and FA are chemically bound on the GO to form the hybrid material.

N-hydroxysuccinimide (NHS) (182.5 mg, 1.6 mmol) and 1-[3-(dimethylamino)propyl]-3-ethylcarbodiimide hydrochloride (EDC) (125 mg, 0.65 mmol), were added to an aqueous suspension (2 cm$^3$) of GO/DEN-OH, and the mixture was ultrasonicated for 2 hours. Then, an aqueous 10 wt % NaHCO$_3$ solution (pH 8) of FA (0.5 wt %, 8 cm$^3$) was added and the mixture was stirred overnight at room temperature. The purification of the product (GO/DEN-OH/FA) was carried out by dialysis against a NaHCO$_3$ solution (pH 8.0) for 48 hours, followed by dialysis against water for 24 hours. Binding of FA on GO was also carried out following the same procedure.

Hybridization of DEN-OH and FA on GO

Figure 2:
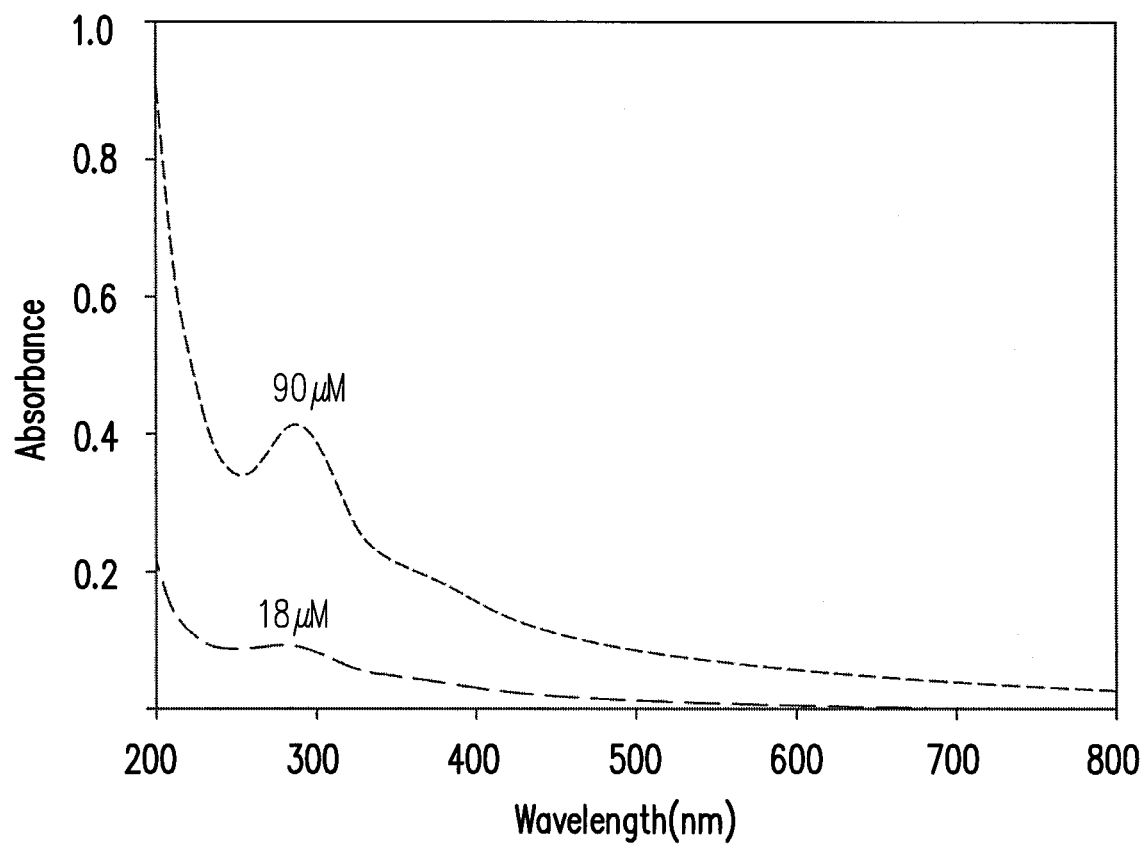
FIG. 2 shows the UV-vis absorption spectra of GO/DEN-OH/FA hybrids having different concentrations of DEN-OH.
Figure 3A:
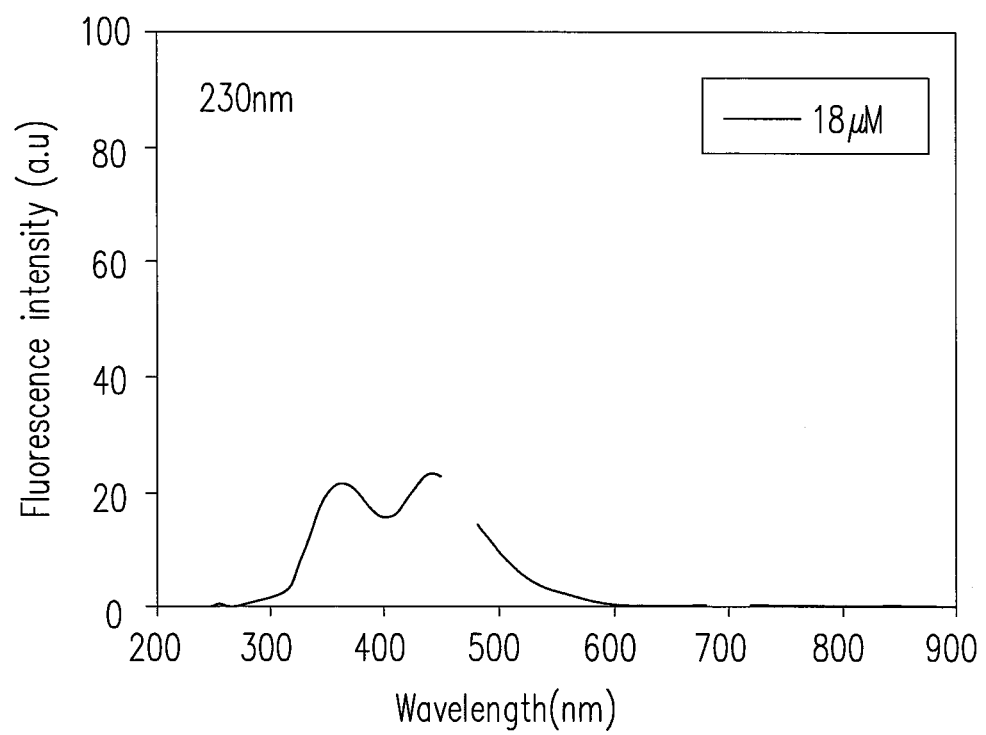
FIGS. 3A-3E shows fluorescence emission spectra of GO/DEN-OH/FA hybrids at different excitation wavelengths.
Figure 3B:
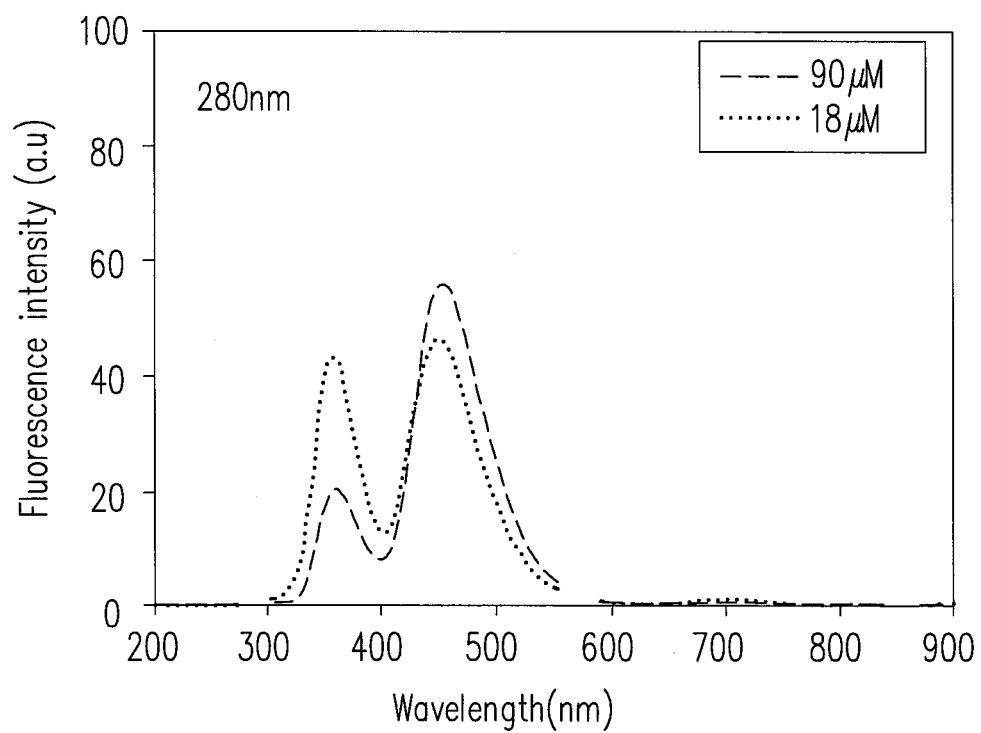
Figure 3C:
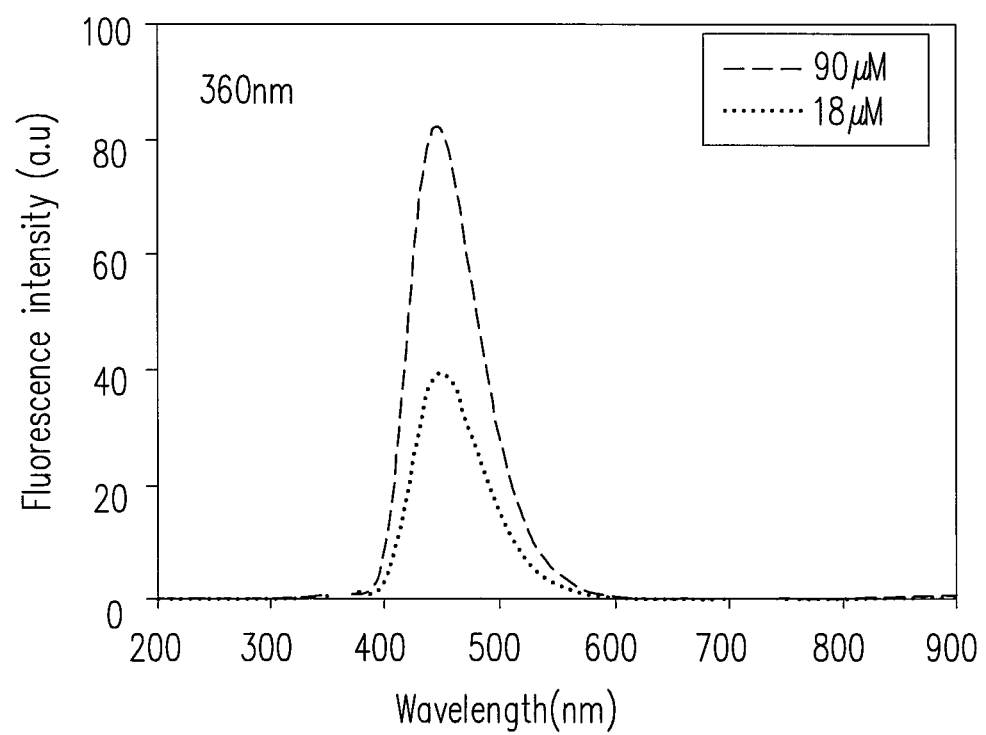
Figure 3D:
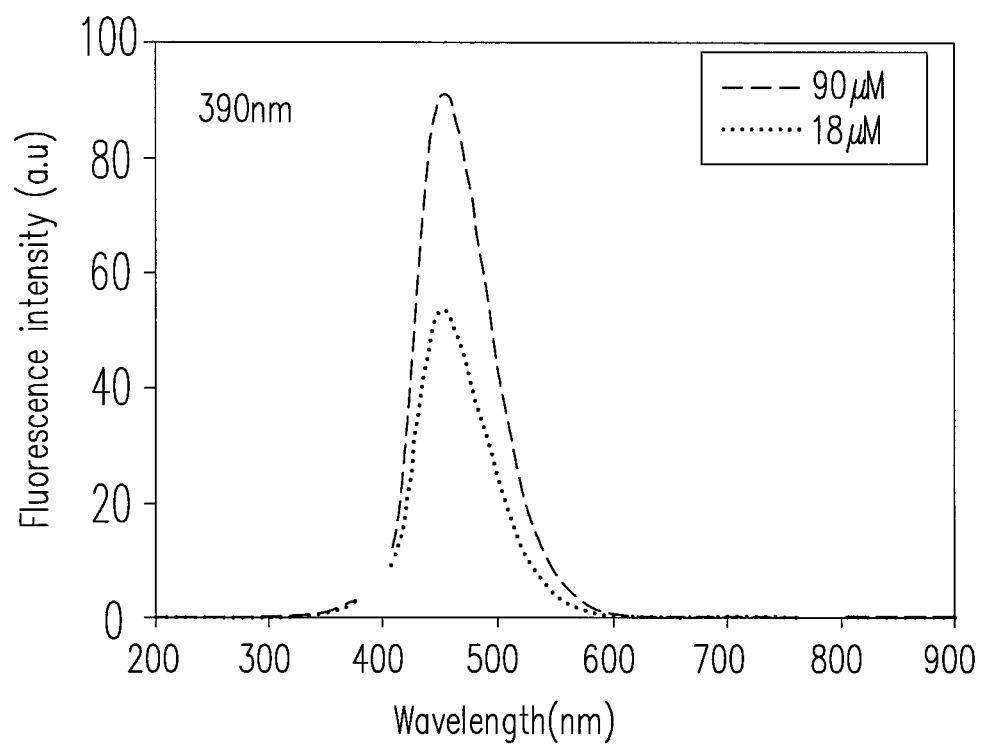
Figure 3E:
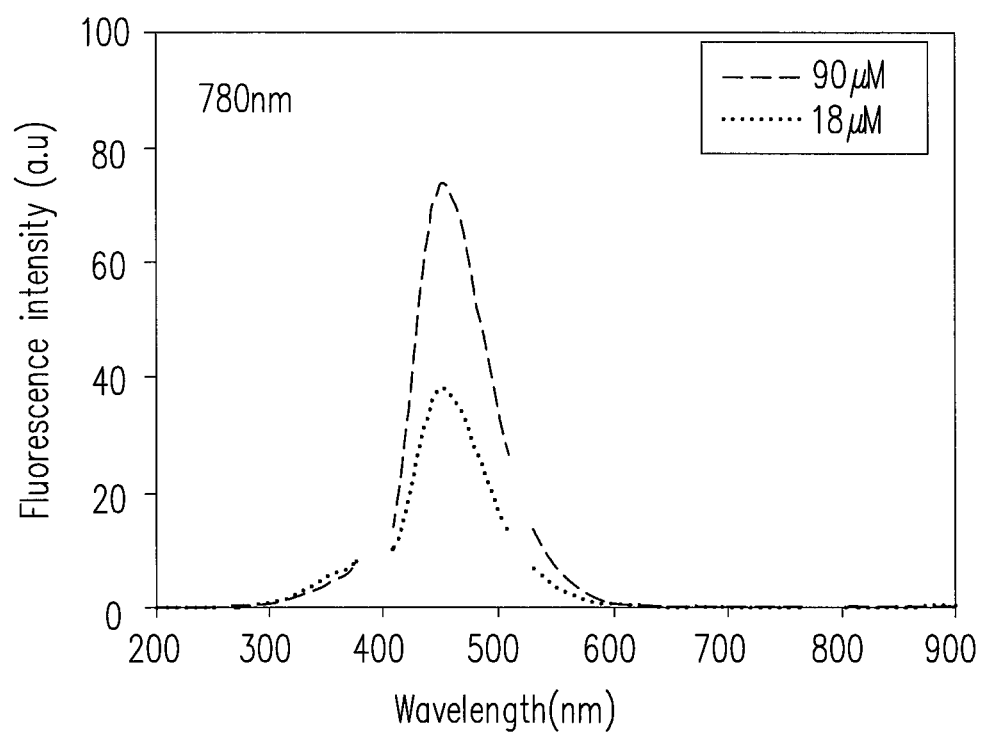

UV-vis absorption spectra of the hybrids of GO/DEN-OH/FA having different concentrations of DEN-OH are shown in FIG. 2. After FA is loaded onto GO/DEN-OH, an absorption band around 280 nm is present, for either GO/DEN-OH/FA hybrid.

Luminescent properties of GO after the immobilization of DEN-OH and folic acid were investigated at different excitation wavelengths. As shown in FIGS. 3A-3E, emission spectra of GO/DEN-OH/FA hybrids having different concentrations of DEN-OH (DEN-OH=18 µM and 90 µM) are shown at different excitation wavelengths. GO/DEN-OH/FA hybrids exhibit emission bands at 355 nm and at 450 nm with comparable intensities at 230 nm and at 280 nm excitation wavelengths. However, GO/DEN-OH/FA hybrids exhibit only one 450 nm emission band at 360 nm, 390 nm and 780 nm excitation wavelengths.

Two-Photon Absorption Properties of GO/DEN-OH/FA Hybrids

Fluorescence emission is the phenomenon of energy release by a molecule that absorbed light or other electromagnetic wave, and the one-photon emission occurs at a longer wavelength than the absorbed light. However, when the absorbed electromagnetic wave is intense, it is possible for one molecule to absorb two photons. This two-photon absorption can lead to the emission at a shorter wavelength than the absorbed electromagnetic wavelength. On the two-photon excitation, a fluorophore is excited by the simultaneous absorption of two less energetic photons, typically in the near infrared range, under the sufficiently intense laser illumination. Because of weak two-photon signals, the two-photon absorption is most often observed by the induced fluorescence. This nonlinear process can occur, if the sum of the energies of two photons is greater than the energy gap between ground and excited states of the molecule. Generally, the two-photon excitation is about twice longer in wavelength than the one-photon excitation.

Figure 4:
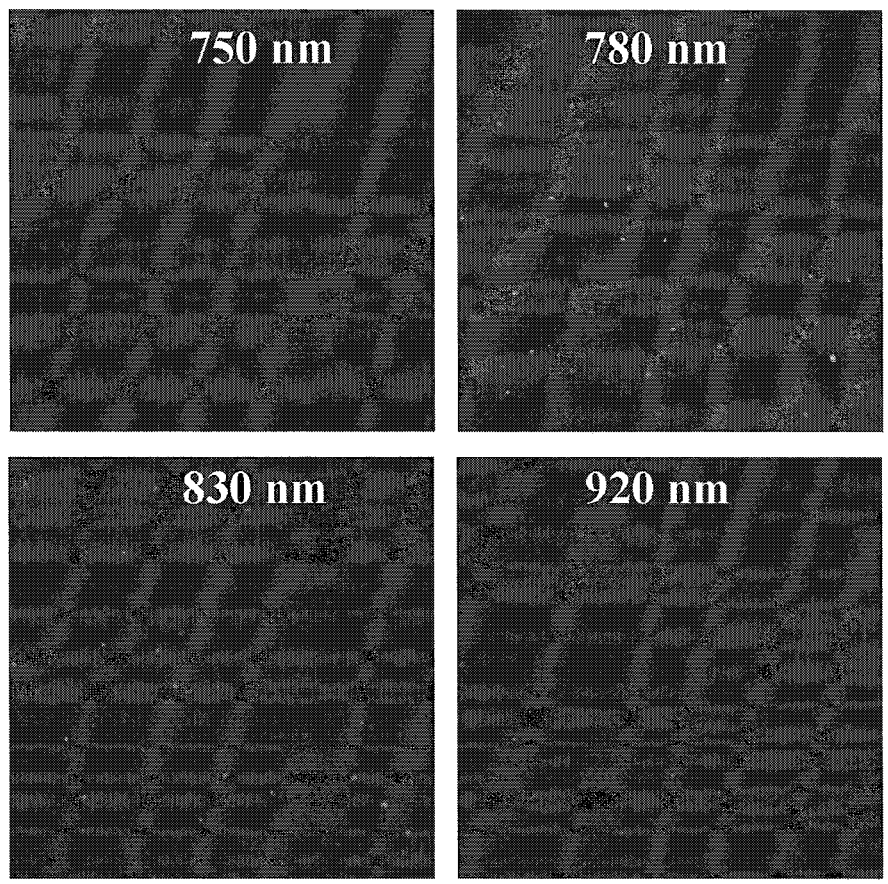
FIG. 4 shows two-photon excited fluorescence images of GO/DEN-OH/FA hybrid (DEN-OH=90 μM) at different excitation wavelengths.
Figure 5:
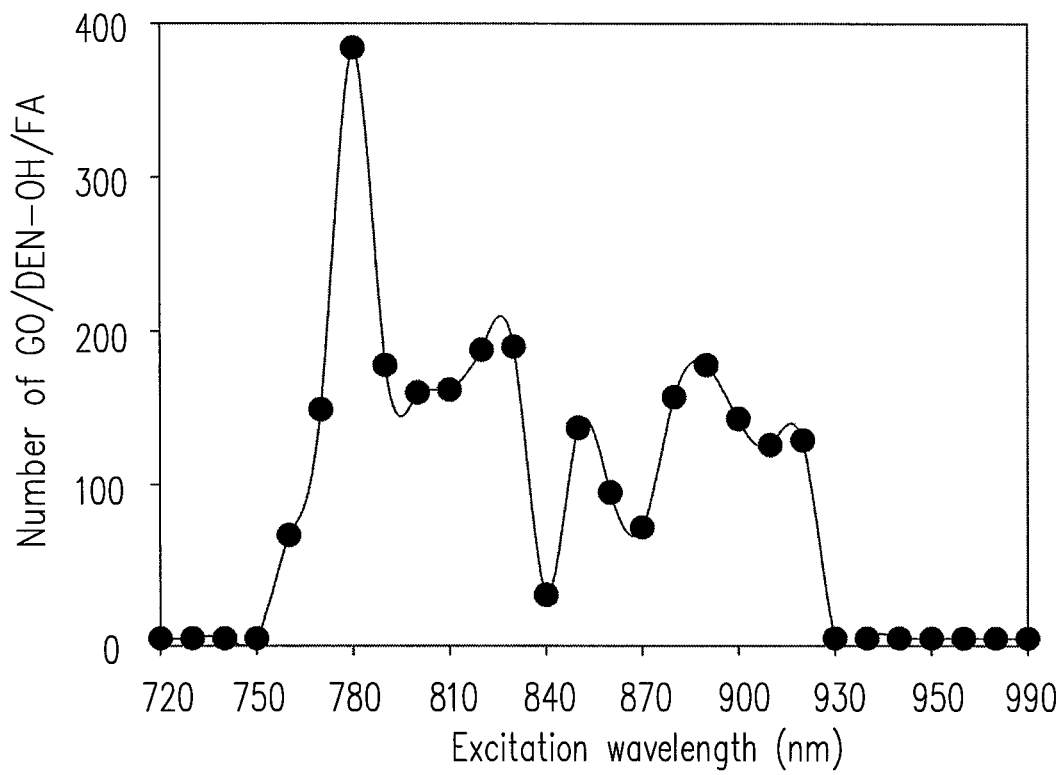
FIG. 5 shows the number of fluorescent GO/DEN-OH/FA hybrid upon two-photon excitation at excitation wavelengths of 720-900 nm.

Two-photon absorption properties of GO/DEN-OH/FA hybrid materials were measured by using a two-photon excitation microscopy at the excitation wavelengths of 720-990 nm to observe the bright fluorescence. Two-photon-excited fluorescence emission images of the GO/DEN-OH/FA hybrid (DEN-OH=90 µM) are shown in FIG. 4, and the number of visible fluorescent GO/DEN-OH/FA upon two-photon excitation were analyzed using an imaging software is shown in FIG. 5. It was observed that the number of visible fluorescent GO/DEN-OH/FA varies in response to different excitation wavelengths, and the GO/DEN-OH/FA hybrid material shows fluorescence emission at 760-920 nm.

On account of the strong fluorescence emission of GO/DEN-OH/FA hybrids in NIR region, GO/DEN-OH/FA hybrids may be function as an imaging agent or a fluorescence marker in biomedical applications. The two-photon absorption phenomenon of GO/DEN-OH/FA hybrids may be exploited and further applied for two-photon fluorescence imaging and/or two-photon photodynamic cancer therapy.

Two-photon absorption properties of GO/DEN-OH/FA hybrid materials are confirmed using fluorescence spectroscopy by the 450 nm emission peak at both of the excitation wavelengths of 390 nm and 780 nm. It confirms that GO/DEN-OH/FA hybrid has strong two-photon absorption properties as it emits fluorescence at a shorter wavelength than the absorbed light.

Efficiency of Photodynamic Therapy with GO/DEN-OH/FA Hybrids

Photodynamic therapy is a noninvasive treatment for many diseases including cancers. Generally, the photodynamic therapy involves the irradiation of visible or near-infrared light at an appropriate wavelength toward the photo-sensitive agent or photosensitizer. Since GO/DEN-OH/FA hybrids possess two-photon absorption properties and are water-dispersible, these hybrids are suitable to be used as the photosensitive agent or photosensitizer for photodynamic therapy. For in-vitro evaluation of photodynamic therapy, the interaction of GO/DEN-OH/FA hybrid to HeLa cells was examined, where folic acid in the hybrid functions as a targeting molecule or ligand to facilitate the hybrid aiming at the HeLa cells. For photodynamic therapy, the use of near-infrared light in the 700-1100 nm range is particularly attractive, because biological systems mostly lack chromophores that absorb the near-infrared light and the near-infrared light is safer than the ultraviolet/visible light for the human body.

Figure 6:
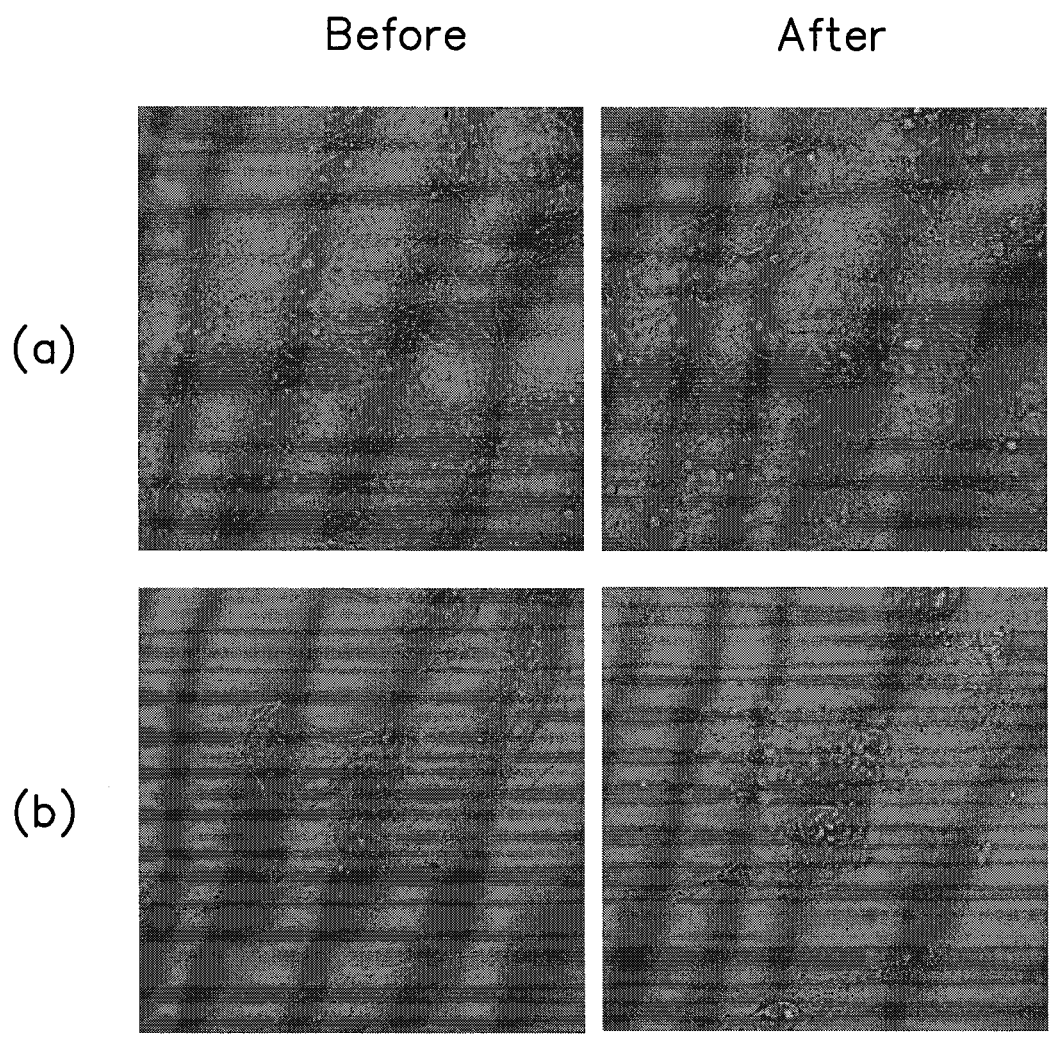
FIG. 6 shows microscopic images of HeLa cells with GO/DEN-OH/FA hybrid and of the control before and after laser irradiation.

The HeLa cells were incubated with GO/DEN-OH/FA hybrid(s) and a laser beam at 780 nm was then irradiated on HeLa cells. The confocal microscopic images before and after irradiation are shown in FIG. 6. In FIG. 6, the images in row (a) were obtained from the control (only HeLa cells) before and after the irradiation, while the images in row (b) were obtained from the HeLa cells incubated with the GO/DEN-OH/FA hybrid (DEN-OH=90 μM) before the irradiation and after irradiation at 780 nm for 15 minutes. While the control was not affected by the laser irradiation, the existence of the photoactive GO/DEN-OH/FA hybrid causes the death of HeLa cells. The cell fatality rate becomes higher as the concentration of DEN-OH in the hybrid increases.

Figure 7:
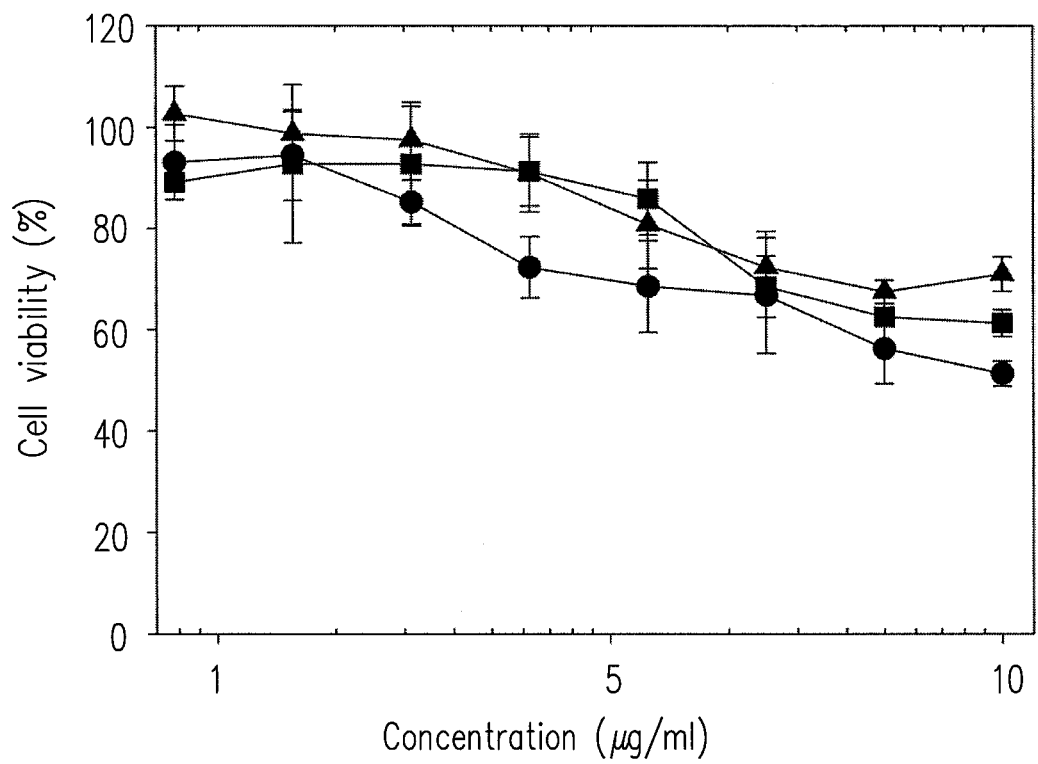
FIG. 7 shows the cell viability as a function of concentration of GO, DEN-OH and GO/DEN-OH/FA hybrid.

The toxicity of GO/DEN-OH/FA hybrids, GO and DEN-OH was evaluated using MTT (3-(4,5-di-methylthiazol-2-yl)-2,5-diphenyltetrazolium bromide, yellow tetrazole) assay and the results are shown in FIG. 7. FIG. 7 shows the cell viability as a function of the concentration of GO (●), DEN-OH (▲) and GO/DEN-OH/FA hybrid (■). The results indicate that the cell viability of GO, DEN-OH and GO/DEN-OH/FA hybrids toward HeLa cells decreases as the concentration increases. However, with the existence of GO/DEN-OH/FA hybrids, enough high viability of HeLa cells is observed. The incubated cells reveal around 80% viability at a GO/DEN-OH/FA hybrid concentration up to 20 μg/ml, indicating a low cytotoxicity.

Generation of Reactive Oxygen Species (ROS) from GO/DEN-OH/FA Hybrids

The excited photosensitizer may lose its energy by emitting light (fluorescence) or by internal conversion into heat. However, the excited photosensitizer may undergo intersystem crossing process and enter into the excited triplet state. The excited-triplet-state photosensitizer can transfer its energy to a neighboring group or molecule and lead to the generation of ROS. The generated ROS can oxidize cellular structure, leading to the damage or fatality of cells.

In order to prove the potential of GO/DEN-OH/FA hybrids in the photodynamic therapy, the ability of GO/DEN-OH/FA hybrids to generate ROS upon laser irradiation at 633 nm was examined by using an aqueous solution of GO/DEN-OH/FA hybrid with N,N'-dimethyl-4-nitrosoaniline (RNO). The oxidation by radical leads to the bleaching of RNO. The bleaching of RNO leads to a strong adsorption band at 440 nm ($\epsilon=3.44\times10^4$ $M^{-1}$ $cm^{-1}$) can be followed quantitatively by using a UV-visible spectrometer. An absorption band of RNO at 440 nm is attributed to mainly a $\pi \rightarrow \pi^*$ charge transfer from ring to nitroso group.

Based on the UV-vis spectra of GO/DEN-OH/FA hybrid solution, the bleaching of RNO was increased almost linearly relative to the increased irradiation time. Hence, GO/DEN-OH/FA hybrids can absorb near-infrared light and generate ROS that can oxidize organelle and cellular structure of HeLa cells and cause the death of HeLa cells. The GO/DEN-OH/FA hybrid material may function as the photosensitizer, leading to the destruction to the target cells, in photodynamic therapy.

In summary, the synthesized GO/DEN-OH/FA hybrids exhibit two photon absorption properties, and the hybrids at the excitation wavelengths of 390 nm and 780 nm show strong fluorescence emission in the visible region at 450 nm. The GO/DEN-OH/FA hybrids also have the ability to generate reactive oxygen species (ROS) upon laser irradiation. It is found that the fluorescence intensities of GO/DEN-OH/FA hybrids are markedly enhanced upon laser irradiation and no quenching of the fluorescence intensities is observed over 2 hours. The damages or fatality (including bleb formation, the shrinkage and the irregularity in shape) of HeLa cells is observed after laser irradiation at 780 nm on HeLa cells that are incubated with GO/DEN-OH/FA hybrids. Satisfactorily low cell cytotoxicity and high biocompatibility have been demonstrated for GO/DEN-OH/FA hybrids at the amount less than 20 μg/ml. These GO/DEN-OH/FA nano-hybrid materials may be used as a fluorescence marker probe in therapeutic applications in tissues and as the photosensitizer in photodynamic therapy for cancer treatments.

The present invention provides GO/DEN-OH/FA hybrid materials of dual functionality. For the medical and/or therapeutic applications, the GO/DEN-OH/FA hybrid material may function as the fluorescence marker or probe and as the attacking agent (drug). That is, the fluorescent GO/DEN-OH/FA hybrid material itself is a completed drug delivery system, since the hybrid material itself functions as the fluorescence marker or probe and as the attacking agent (drug) at the same time, with no additional therapeutic agents.

As there is no need to use the fluorescence marker or label for the fluorescent GO/DEN-OH/FA hybrid material, the cytotoxicity and water solubility may be further enhanced. Due to its strong fluorescence emission, the hybrid material may also function as an imaging agent for fluorescence imaging. Additionally, the GO/DEN-OH/FA hybrid material may be used as a drug delivery system for additional therapeutic agents.

While the invention has been described and illustrated with reference to specific embodiments thereof, these descriptions and illustrations do not limit the invention. It should be understood by those skilled in the art that various changes may be made and equivalents may be substituted without departing from the true spirit and scope of the invention as defined by the appended claims. The illustrations may not be necessarily being drawn to scale. There may be distinctions between the artistic renditions in the present disclosure and the actual apparatus due to manufacturing processes and tolerances. There may be other embodiments of the present invention which are not specifically illustrated. The specification and the drawings are to be regarded as illustrative rather than restrictive. Modifications may be made to adapt a particular situation, material, composition of matter, method, or process to the objective, spirit and scope of the invention. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the invention.

What is claimed is:

1. A hybrid material, comprising 50-256 parts by weight of a hydroxyl-terminated poly(amidoamine) dendrimer, 9 parts by weight of folic acid and 11 parts by weight graphene oxide based on a total of the hybrid material, wherein the hydroxyl-terminated poly(amidoamine) dendrimer and the folic acid are each individually and directly bound to and chemically bound on the graphene oxide to form the hybrid material.

2. The material of claim 1, wherein the hybrid material exhibits two photon absorption by showing fluorescence emission of a first wavelength that is obtained at excitation wavelengths of a second wavelength and a third wavelength, wherein the second wavelength is shorter than the first wavelength and the third wavelength is longer than the first wavelength.

3. The material of claim 2, wherein the first wavelength is 450 nm, the second wavelength is 390 nm and the third wavelength is 780 nm.

4. The material of claim 1, wherein the hybrid material absorbs near-infrared light and generates reactive oxygen species (ROS) upon radiation.

5. The material of claim 1, wherein the hybrid material is water dispersible.

6. The material of claim 1, wherein the hydroxyl-terminated poly(amidoamine) dendrimer is a fourth-generation hydroxyl-terminated poly(amidoamine) dendrimer.

7. The material of claim 1, wherein the hybrid material functions as a fluorescence marker.

8. The material of claim 1, wherein the hybrid material functions as an attacking drug in photodynamic therapy.

9. The material of claim 1, wherein the hybrid material has a relative ratio of the graphene oxide:the hydroxyl-terminated poly(amidoamine) dendrimer:the folic acid being 11:50:9 by weight for the hybrid material having a concentration of the hydroxyl-terminated poly(amidoamine) dendrimer of 18 µM.

10. The material of claim 1, wherein the hybrid material has a relative ratio of the graphene oxide:the hydroxyl-terminated poly(amidoamine) dendrimer:the folic acid being 11:256:9 by weight for the hybrid material having a concentration of the hydroxyl-terminated poly(amidoamine) dendrimer of 90 µM.

11. A hybrid material, comprising at least a hydroxyl-terminated fourth-generation poly(amidoamine) dendrimer and folic acid each individually and directly bound to and chemically bound on graphene oxide to form the hybrid material, wherein the hybrid material is prepared by mixing the hydroxyl-terminated poly(amidoamine) dendrimer and the graphene oxide by stirring at room temperature, adding N,N'-dicyclohexylcarbodiimide (DCC) and 4-dimethylaminopyridine (DMAP) to the mixture of the hydroxyl-terminated poly(amidoamine) dendrimer and the graphene oxide by stirring at room temperature for esterification to form an intermediate GO/DEN-OH that is they hydroxyl-terminated poly(amidoamine) dendrimer bound on the graphene oxide, adding N-hydroxysuccinimide (NHS) and 1-[3-(dimethylamino)propyl]-3-ethylcarbodiimide hydrochloride (EDC) to an aqueous suspension of the intermediate GO/DEN-OH, and then adding the folic acid to the mixture of NHS, EDC and the aqueous suspension of the intermediate GO/DEN-OH by stirring at room temperature to obtain the hybrid material.

* * * * *